(12) United States Patent
Shiraki et al.

(10) Patent No.: US 8,460,523 B2
(45) Date of Patent: Jun. 11, 2013

(54) ANALYSIS INSTRUMENT

(75) Inventors: Yasunori Shiraki, Kyoto (JP); Yasuhide Kusaka, Kyoto (JP); Taizo Kobayashi, Kyoto (JP)

(73) Assignee: Arkray, Inc., Kyoto-Shi (JP)

( * ) Notice: Subject to any disclaimer, the term of this patent is extended or adjusted under 35 U.S.C. 154(b) by 1152 days.

(21) Appl. No.: 10/537,708

(22) PCT Filed: Dec. 1, 2003

(86) PCT No.: PCT/JP03/15358
§ 371 (c)(1),
(2), (4) Date: Jun. 2, 2005

(87) PCT Pub. No.: WO2004/051249
PCT Pub. Date: Jun. 17, 2004

(65) Prior Publication Data
US 2006/0042943 A1 Mar. 2, 2006

(30) Foreign Application Priority Data
Dec. 2, 2002 (JP) .................................. 2002-350198

(51) Int. Cl.
*G01N 33/487* (2006.01)
(52) U.S. Cl.
USPC ............ 204/403.01; 204/403.02; 204/403.03; 204/403.09; 205/775
(58) Field of Classification Search
USPC ........ 204/403.1–403.15; 205/775, 777.5–778; 422/55–57
See application file for complete search history.

(56) References Cited

U.S. PATENT DOCUMENTS

| | | | |
|---|---|---|---|
| 5,264,103 A * | 11/1993 | Yoshioka et al. | 205/778 |
| 5,320,732 A | 6/1994 | Nankai et al. | |
| 5,354,447 A | 10/1994 | Uenoyama et al. | |
| 5,438,271 A * | 8/1995 | White et al. | 324/444 |
| 5,916,156 A | 6/1999 | Hildenbrand et al. | |
| 5,980,708 A * | 11/1999 | Champagne et al. | 204/406 |
| 6,004,441 A | 12/1999 | Fujiwara et al. | |
| 6,125,292 A * | 9/2000 | Uenoyama et al. | 435/14 |
| 6,258,229 B1 | 7/2001 | Winarta et al. | |
| 6,287,451 B1 * | 9/2001 | Winarta et al. | 205/777.5 |
| 6,572,745 B2 * | 6/2003 | Rappin et al. | 204/403.14 |
| 6,599,406 B1 * | 7/2003 | Kawanaka et al. | 204/403.02 |
| 6,743,635 B2 * | 6/2004 | Neel et al. | 436/95 |
| 6,858,433 B1 * | 2/2005 | Zivitz | 436/151 |
| 6,875,327 B1 | 4/2005 | Miyazaki et al. | |
| 6,960,287 B2 * | 11/2005 | Charlton | 205/775 |

(Continued)

FOREIGN PATENT DOCUMENTS

| EP | 1024358 A1 | 8/2000 |
|---|---|---|
| EP | 1074832 A1 | 2/2001 |

(Continued)

*Primary Examiner* — Keith Hendricks
*Assistant Examiner* — Bach Dinh
(74) *Attorney, Agent, or Firm* — Fox Rothschild LLP

(57) ABSTRACT

The present invention relates to an analytical tool (X1) to be mounted to an analytical apparatus (1) which includes a plurality of terminals (11, 12) and an analysis circuit (13). The analytical tool includes a plurality of electrodes (21, 22) coming into contact with the plurality of terminals (11, 12) when mounted to the analytical apparatus (1). In the analytical tool (X1), at least one (12) of the electrodes (21, 22) serves as a disturbing-noise countermeasure electrode to which disturbing noise is more likely to come in comparison with the other electrodes (11) than the above-mentioned electrode (12).

1 Claim, 11 Drawing Sheets

U.S. PATENT DOCUMENTS

| | | |
|---|---|---|
| 7,651,595 B2 * | 1/2010 | Doi et al. .................. 204/400 |
| 2002/0157947 A1 | 10/2002 | Rappin et al. |
| 2003/0196894 A1 * | 10/2003 | Cai et al. ................ 204/403.01 |
| 2003/0203498 A1 * | 10/2003 | Neel et al. .................... 436/95 |
| 2004/0055885 A1 * | 3/2004 | Yamamoto et al. ...... 204/403.01 |
| 2004/0134779 A1 * | 7/2004 | Hsu et al. ................ 204/403.03 |
| 2004/0178066 A1 * | 9/2004 | Miyazaki et al. ........ 204/403.01 |
| 2004/0178067 A1 | 9/2004 | Miyazaki et al. |
| 2006/0042942 A1 * | 3/2006 | Oura et al. .............. 204/403.01 |

FOREIGN PATENT DOCUMENTS

| | | |
|---|---|---|
| EP | 1143245 A2 | 10/2001 |
| JP | 60058541 A | 4/1985 |
| JP | 2-310457 | 12/1990 |
| JP | 4-357449 | 12/1992 |
| JP | 5-164724 | 6/1993 |
| JP | 8-2609 | 1/1996 |
| JP | 8-10208 | 1/1996 |
| JP | 9-189675 | 7/1997 |
| JP | 2001-208715 | 8/2001 |
| JP | 2003-501626 | 1/2003 |
| WO | 9429705 A1 | 12/1994 |
| WO | WO99/05516 * | 4/1999 |
| WO | WO01/36953 * | 5/2001 |
| WO | 0171328 A1 | 9/2001 |
| WO | 03091717 A1 | 11/2003 |

* cited by examiner

ANALYSIS INSTRUMENT

TECHNICAL FIELD

The present invention relates to an analysis instrument used for analyzing a particular component in a sample, and in particular to an analytical tool used for measuring e.g. a glucose level.

BACKGROUND ART

In a typical method for measuring a blood glucose level, redox reaction is utilized. Meanwhile, portable handheld blood glucose level measuring apparatuses are widely used so that the blood glucose level can be measured easily at home or away from home. In such a portable blood glucose level measuring apparatus, the blood glucose level is measured by mounting a disposable biosensor for providing an enzymatic reaction field to the apparatus and supplying blood to the biosensor.

The measurement of a blood glucose level may be performed by utilizing an electrochemical technique. In such a case, the blood glucose level is measured by mounting a biosensor 90 to a blood glucose level measuring apparatus 91 in such a manner as shown in FIG. 14 (See JP-B-H8-10208, for example). The biosensor 90 includes an insulating substrate 92 formed with a first and a second electrodes 93 and 94 for applying voltage to the enzymatic reaction field. The blood glucose level measuring apparatus 91 comprises a connector 97 including a first and a second terminals 95 and 96 coming into contact with the first and the second electrodes 93 and 94, and a measurement circuit 98 for determining the blood glucose level based on the information from the connector 97.

The blood glucose level measuring apparatus is affected by various disturbing noise. The disturbing noise may influence the measurement result or destroy the electronic part to make the measurement impossible. Particularly, a portable small measurement apparatus is liable to be influenced by static electricity from a human body. Specifically, since the biosensor 90 is usually mounted to the blood glucose level measuring apparatus 91 manually, the static electricity, if built up in the human body, is discharged to the first and the second electrodes 93 and 94 of the biosensor 90 or the first and the second terminals 95 and 96 of the blood glucose level measuring apparatus 91. If no countermeasure is taken against the static electricity, the static electricity is inputted, as disturbing noise, into the measurement circuit 98 through the first electrode 93 and the first terminal 95, for example. Therefore, as the conventional measures to reduce the influence of static electricity, the arrangement of the first and the second terminals 95 and 96 in the blood glucose level measuring apparatus 91 has been contrived or the withstand voltage of each electronic part constituting the measurement circuit 98 has been increased. In another method to cope with static electricity, a conductive sheet is disposed adjacent to the connector or the nearby portion (See JP-Y-H8-2609, for example).

However, the above-described conventional countermeasures against disturbing noise are realized by modifying the design of the blood glucose level measuring apparatus 91. Therefore, such countermeasures complicate the structure of the blood glucose level measuring apparatus 91 and increase the size of the apparatus, and hence, increase the manufacturing cost.

Recently, there is a tendency to reduce the thickness of the first and the second electrodes 93 and 94 to reduce the manufacturing cost of the biosensor 90. Further, to adapt the biosensor 90 to the portable blood glucose level measuring apparatus 91, the size of the biosensor 90, including the size of the first and the second electrodes 93 and 94, cannot help being reduced. In such cases, the resistance of the first and the second electrodes 93 and 94 increases. Therefore, in the circuit structure shown in FIG. 14, for example, Joule heat is generated adjacent to the contact point between the first electrode 93 and the first terminal 95 of the blood glucose level measuring apparatus 91 when static electricity tries to move through the contact point. When the generated Joule heat is high, the first electrode 93 may melt. In such a case, the biosensor 90 mounted to the apparatus cannot measure the blood glucose level. Further, the melt of the first electrode 93 of the biosensor 90 adheres to the first terminal 95 of the blood glucose level measuring apparatus 91 and changes the resistance of the first terminal 95, so that an error is generated in the subsequent measurement of responsive current. Such a problem is more significant as the thickness of the first electrode 93 is made smaller.

DISCLOSURE OF THE INVENTION

An object of the present invention is to provide an analytical tool which is capable of cost-effectively reducing the influence of disturbing noise such as static electricity even when the thickness of the electrodes of the analytical tool is reduced and without increasing the size of the analytical apparatus for analyzing a sample by using the analytical tool.

According to the present invention, there is provided an analytical tool to be mounted to an analytical apparatus which includes a plurality of terminals and an analysis circuit. The analytical tool includes a plurality of electrodes coming into contact with the plurality of terminals when mounted to the analytical apparatus. At least one of the electrodes serves as a disturbing-noise countermeasure electrode to which disturbing noise is more likely to come in comparison with the other electrodes than the above-mentioned one electrode.

For example, the plurality of electrodes include a first electrode to be connected to the analysis circuit, and a second electrode for applying voltage to a target portion in cooperation with the first electrode. In this case, the second electrode can serves as the disturbing-noise countermeasure electrode.

The second electrode is not electrically connected to the analysis circuit when the analytical tool is mounted to the analytical apparatus. More specifically, the second electrode is brought into contact with a ground connection terminal when the analytical tool is mounted to the analytical apparatus.

The plurality of electrodes may include a third electrode which is not involved in the voltage application to the target portion, in addition to the first electrode and the second electrodes. In this case, the third electrode can serve as the disturbing-noise countermeasure electrode.

For example, the third electrode is not electrically connected to the analysis circuit when the analytical tool is mounted to the analytical apparatus. Specifically, the third electrode is brought into contact with a ground connection terminal when the analytical tool is mounted to the analytical apparatus.

In the analytical tool of the present invention, both of the second and the third electrodes may serve as the disturbing-noise countermeasure electrodes. In this case, similarly to the foregoing cases, the second and the third electrodes are not electrically connected to the analysis circuit but brought into contact with e.g. the ground connection terminal when the analytical tool is mounted to the analytical apparatus.

The analytical tool according of the present invention further comprises a flow path for moving a sample, and an air vent for discharging air from the flow path. Preferably, in this case, the disturbing-noise countermeasure electrode includes an input portion to which disturbing noise coming through the air vent is inputted. For example, the input portion faces the air vent at least partially. Specifically, the input portion is provided directly below the air vent and covered by an insulating film including an opening. In this case, by the opening of the insulating film, the input portion is partially exposed via the air vent.

The analytical tool according to the present invention may further comprise a substrate on which the plurality of electrodes are formed, and a cover which is bonded to the substrate and in which the air vent is formed. In this case, in plan view, the input portion includes a part located at the periphery of the air vent. Preferably, in plan view, the input portion surrounds the air vent.

Preferably, the disturbing-noise countermeasure electrode surrounds at least one of the rest of the electrodes. The disturbing-noise countermeasure electrode may be formed along the periphery of the substrate.

In the analytical tool of the present invention, it is preferable that, in mounting the analytical tool to the analytical apparatus, the disturbing-noise countermeasure electrode comes into contact with a corresponding one of the terminals of the analytical apparatus earlier than the rest of the electrodes. Specifically, the disturbing-noise countermeasure electrode includes a portion located on the substrate at a position closer to an insertion edge of the substrate (the edge of the substrate on the insertion direction side with respect to the analytical apparatus) than the rest of the electrodes.

Preferably, the analytical tool of the present invention further comprises a pinch portion which is utilized in mounting the analytical tool to the analytical apparatus or detaching the analytical tool from the analytical apparatus.

Preferably, in this case, the disturbing-noise countermeasure electrode is covered by an insulating film while being exposed at a portion adjacent to the pinch portion.

For example, the pinch portion comprises a recess which is inwardly sunk in a plan view of the analytical tool.

BEST MODE FOR CARRYING OUT THE INVENTION

A first through a sixth embodiments of the present invention will be described below with reference to the accompanying drawings.

First, with reference to FIG. 1 through FIG. 7, the first embodiment of the present invention will be described.

Figure 1:
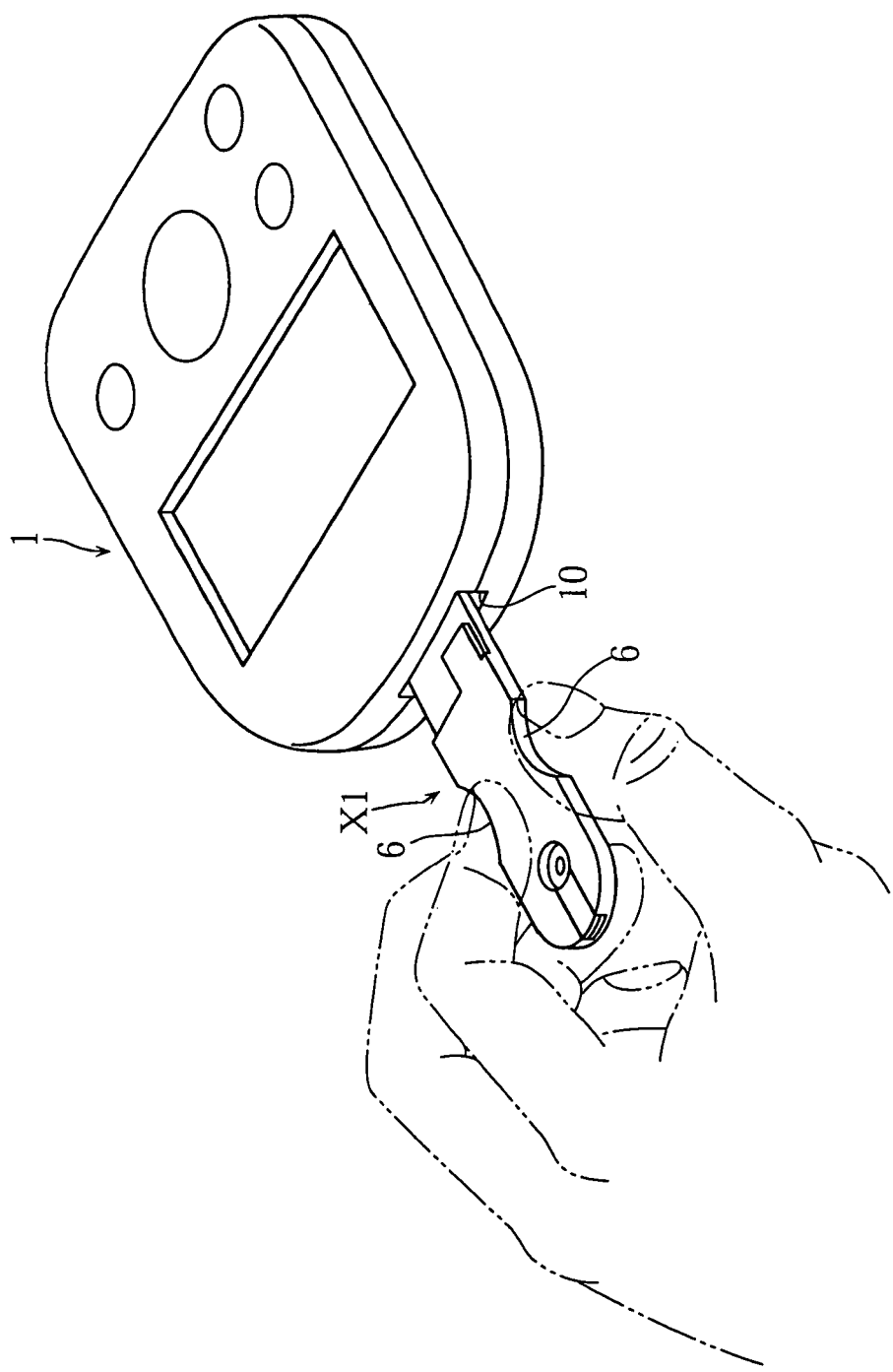
FIG. 1 an overall perspective view showing the state in which a biosensor according to a first embodiment of the present invention is mounted to an analytical apparatus.
Figure 2:
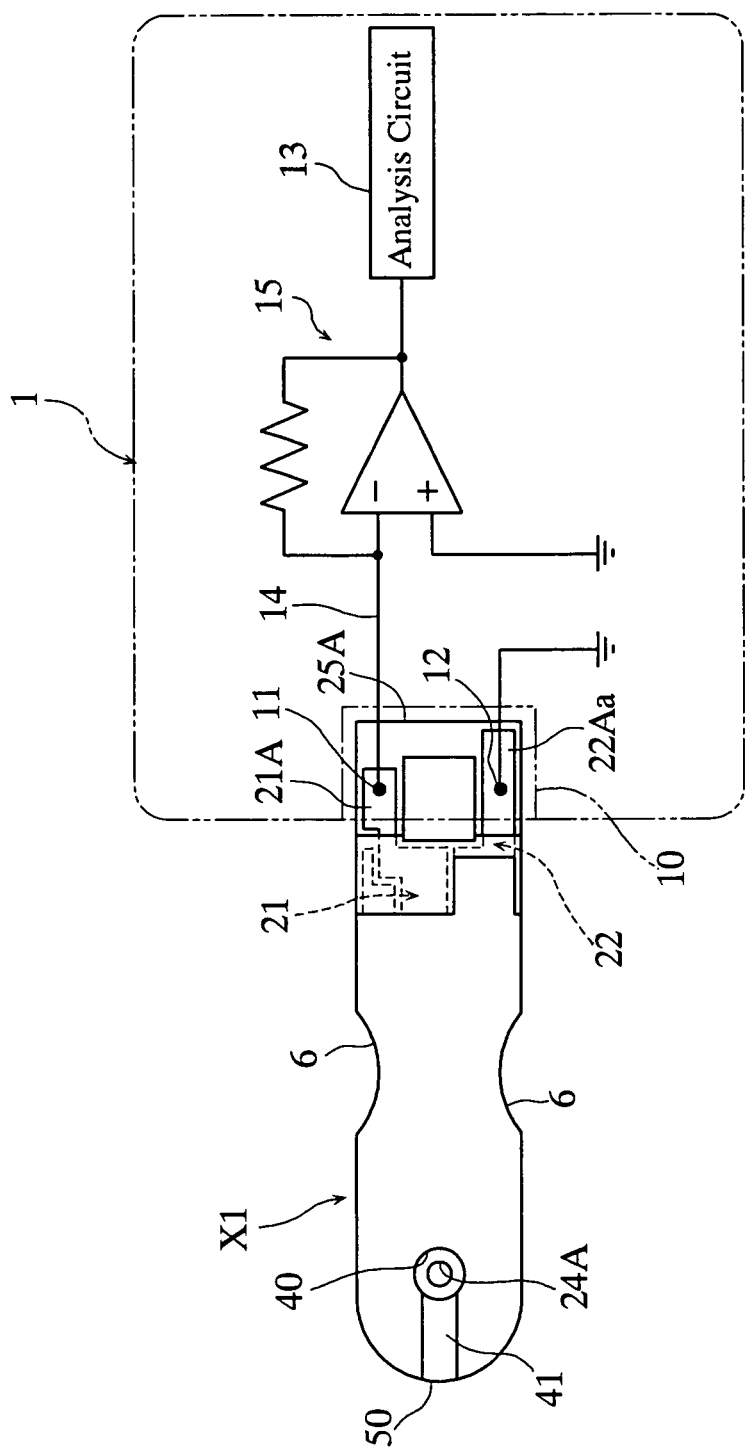
FIG. 2 illustrates the state of FIG. 1, showing the biosensor in plan and the analytical apparatus in block diagram.
Figure 3:
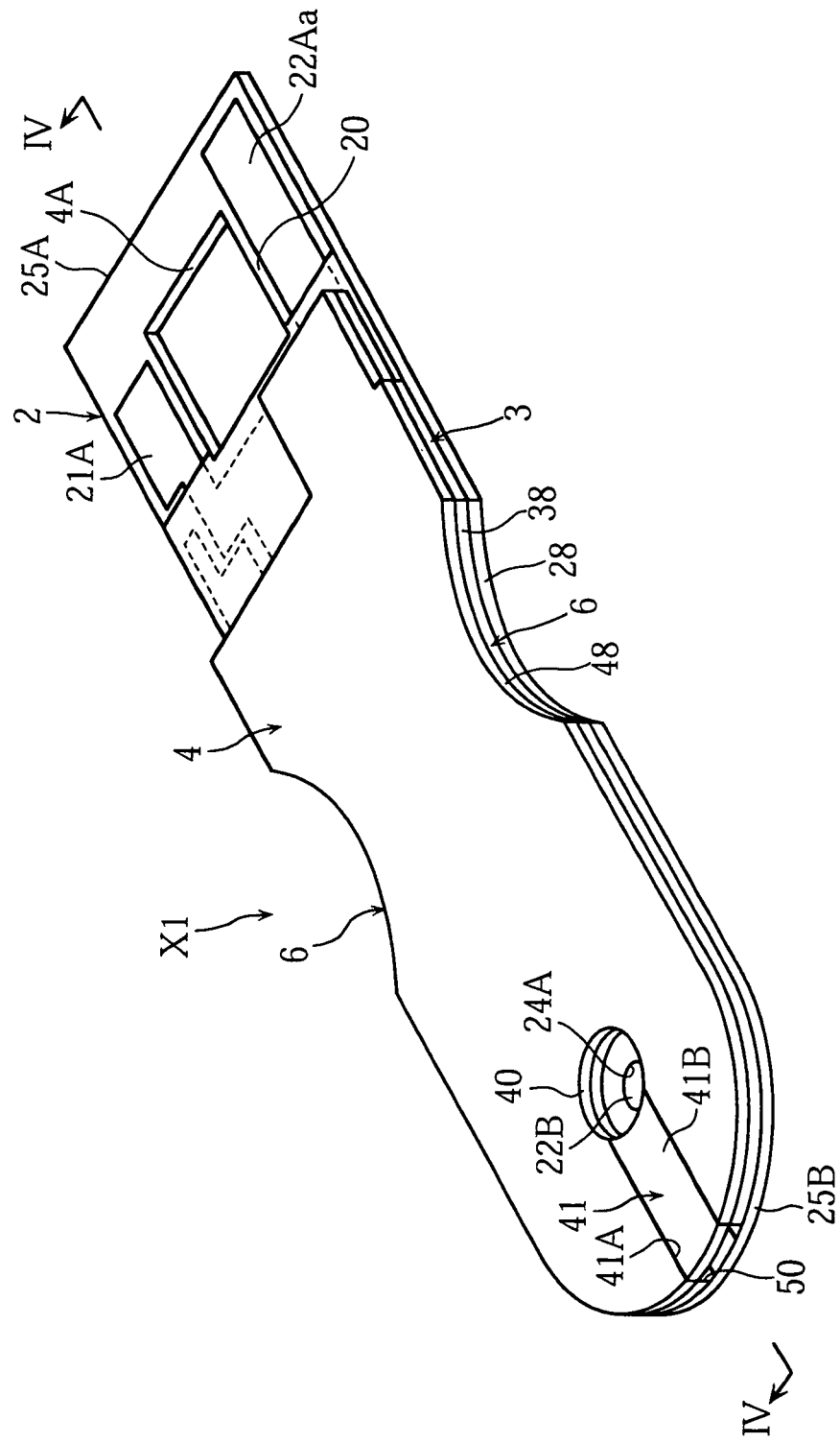
FIG. 3 is an overall perspective view of the biosensor shown in FIGS. 1 and 2.
Figure 4:
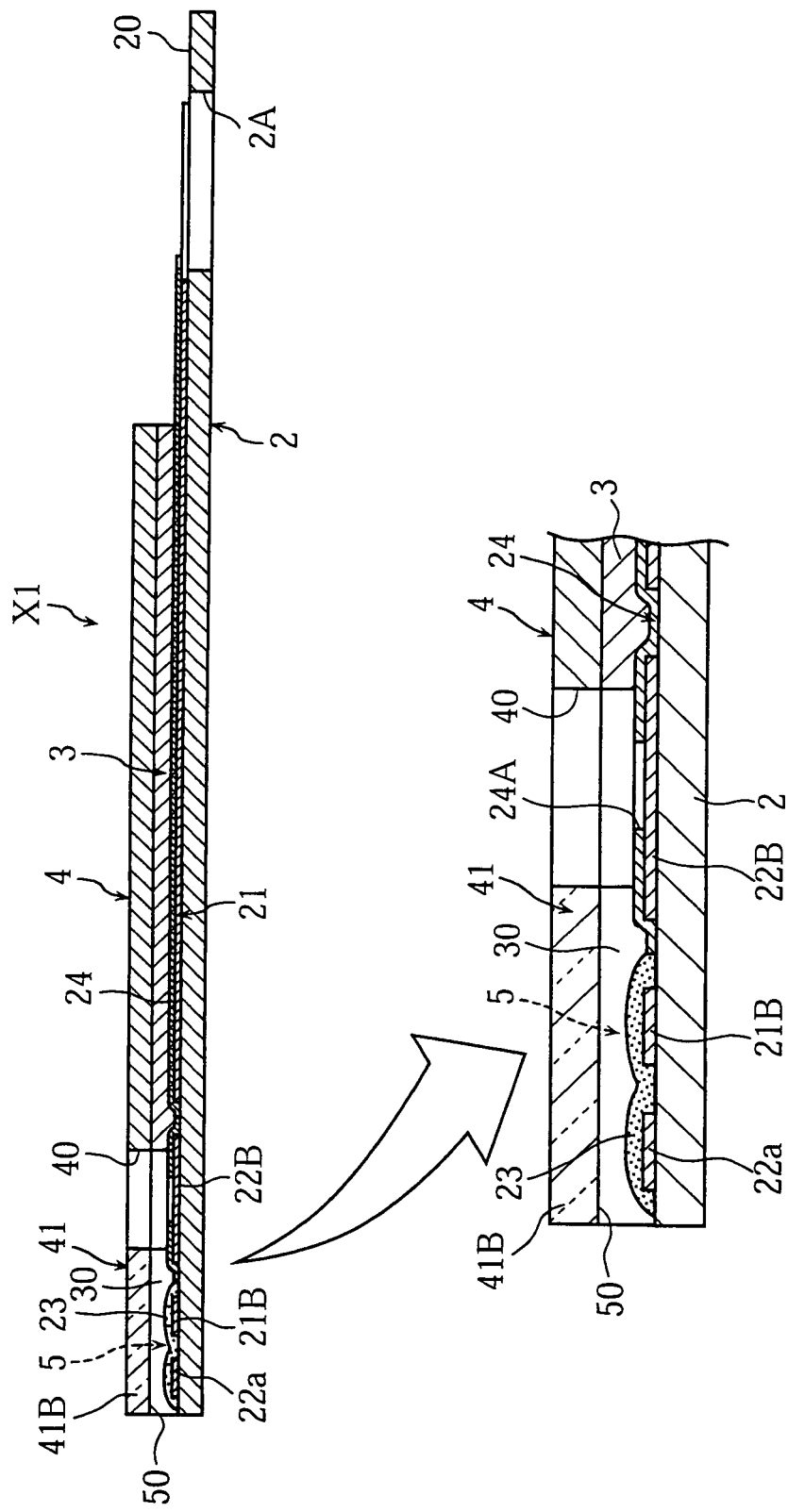
FIG. 4 is a sectional view taken along lines IV-IV in FIG. 3, with the principal portion shown as enlarged.

FIGS. 1 and 2 show a disposable biosensor X1 arranged to be set into a connector 10 of an analytical apparatus 1 in use. As shown in FIGS. 3 and 4, the biosensor X1 has a plate-like configuration that includes a substrate 2 and a cover 4 stacked on the upper surface 20 of the substrate via a spacer 3. A flow path 5 and a pinch portion 6 are formed in the assembly of the above elements 2-4.

Figure 5:
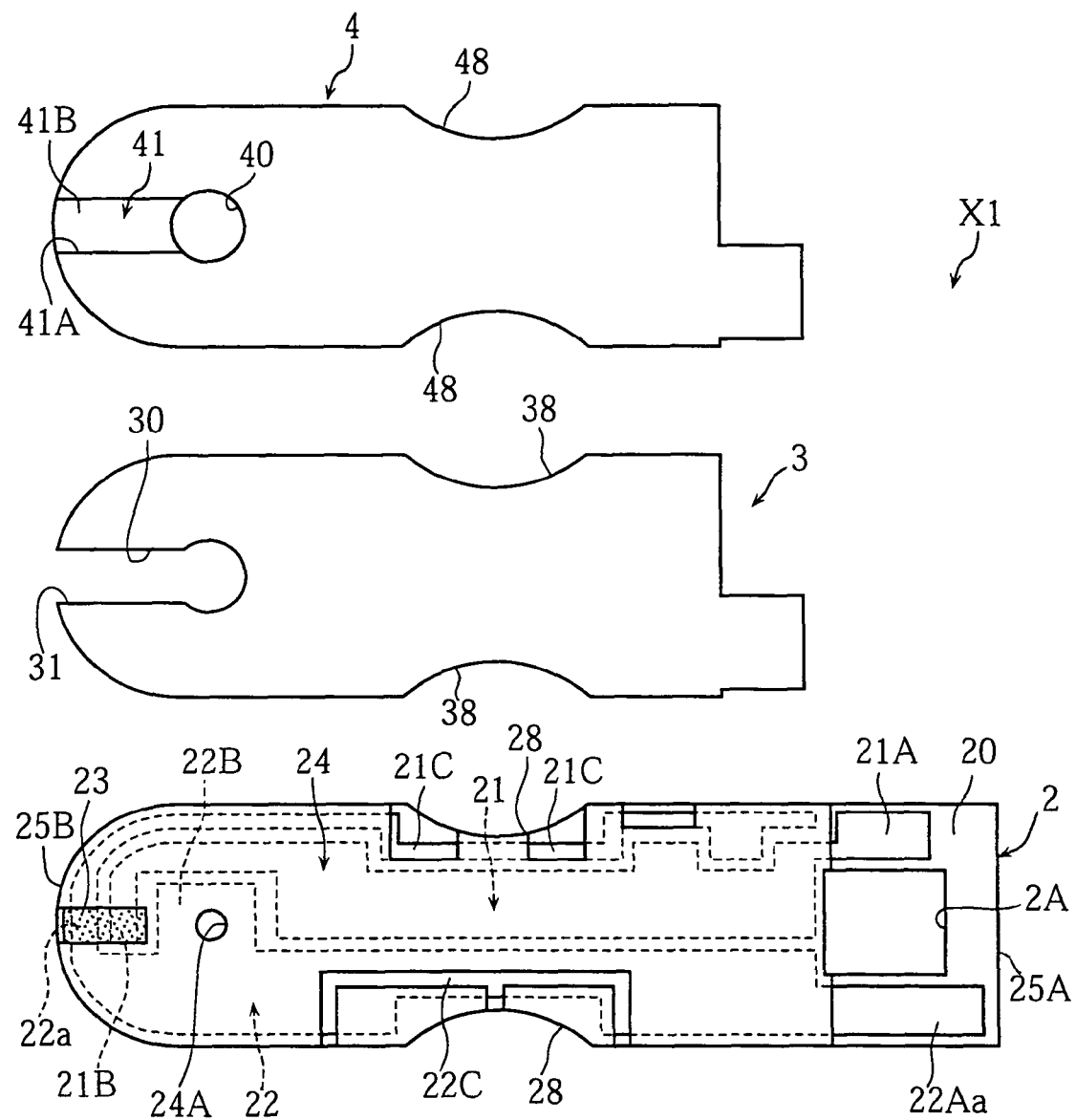
FIG. 5 is a plan view showing the disassembled state of the biosensor shown in FIG. 3.

The spacer 3 determines the dimensions of the flow path 5, and is formed, as shown in FIG. 5, with a slit 30 having an open front end. The slit 30 defines the width and the length of the path 5. The open front end 31 of the slit 30 provides a sample inlet 50 for introducing a sample into the path 5.

As shown in FIG. 3 through FIG. 5, the cover 4 includes an air vent 40 and a window 41. As seen from FIG. 4, the air vent 40, provided for discharging air in the flow path 5 to the outside, communicates with the interior of the flow path 5. The window 41 is utilized for checking whether or not the sample has been introduced into the flow path 5 and also for checking the movement of the sample in the flow path 5. In a plan view of the biosensor X1, the window is disposed between the sample inlet 50 and the air vent 40. The window 41 may be provided by producing a cutout in the cover 4 and then fitting a transparent member 41B into the cutout 41A.

Figure 6:
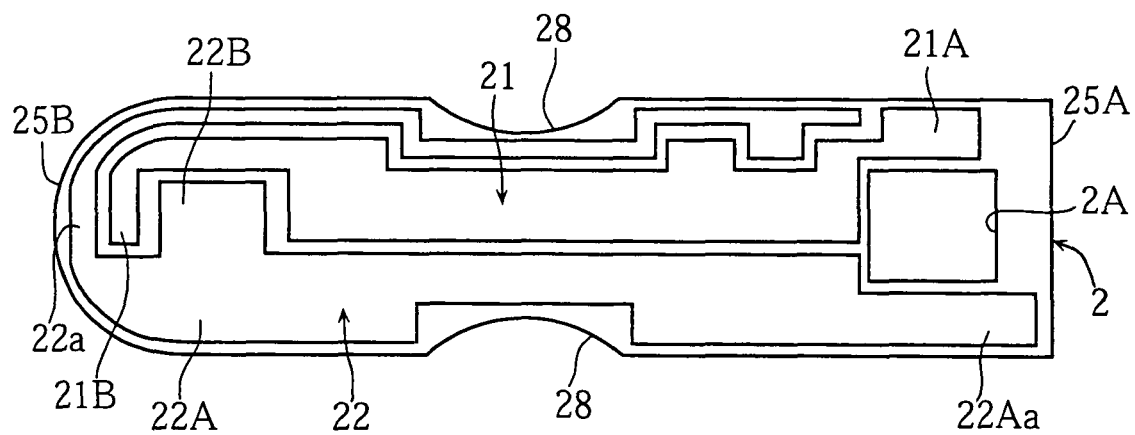
FIG. 6 is a plan view for illustrating the working electrode and the counter electrode of the biosensor.

As shown in FIGS. 5 and 6, the substrate 2 is made of an insulating material into a configuration elongated in one direction (longitudinal direction), and is formed with a through-hole 2A at a portion which is not covered by the cover 4. The through-hole 2A provides the analytical apparatus 1 (See FIGS. 1 and 2) with information on the biosensor X1, such as lot information. In the analytical apparatus 1, the lot information can be obtained from checking certain facts, for example, whether the through-hole exists or not, or what size the hole has, or at what position the hole is located. The upper surface 20 of the substrate 2 is formed with a working electrode 21, a counter electrode 22, a reagent portion 23 and an insulating film 24.

The working electrode 21 cooperates with the counter electrode 22 to apply a voltage to the reaction area or field. The working electrode 21, as a whole, extends in the longitudinal direction of the substrate 2. The working electrode 21 has an end 21A adjacent to a shorter edge 25A of the substrate 2. When the biosensor X1 is mounted to the analytical apparatus 1, the end 21A comes into contact with a first terminal 11 of the analytical apparatus 1, which will be described later (See FIG. 2). The working electrode 21 has another end 21B, which is adjacent to an arcuate edge 25B of the substrate 2 and extends in the widthwise direction of the substrate 2.

The counter electrode 22, serving as countermeasures against disturbing noise, includes a main line portion 22A and an island portion 22B projecting from the main line portion 22A, the main line portion being in the form of a hairpin extending along the periphery of the substrate 2. The counter electrode 22 generally encloses the working electrode 21, with the end 21B of the working electrode 21 positioned between a corner region 22a of the main line portion 22A and the island portion 22B. The main line portion 22A has an end 22Aa located adjacent to the shorter edge 25A of the substrate 2. When the biosensor X1 is mounted to the analytical apparatus 1, the end 22Aa comes into contact with a second terminal 12, described below, of the analytical apparatus 1, the end being positioned closer to the shorter edge 25A of the substrate 2 than the end 21A of the working electrode 21 (See FIG. 2). In the plan view of the biosensor X1, the island portion 22B is positioned directly below the air vent 40, and its plan-view area is larger than that of the air vent 40.

The reagent portion 23 is so formed as to bridge between the end 21B of the working electrode 21 and the corner region 22a of the main line portion 22A. The reagent portion 23 is in a solid state containing an oxidoreductase and an electron mediator, for example, but can dissolve when a sample is supplied thereto. The kinds of the oxidoreductase and the electron mediator to be used depend on e.g. the kind of the component to be measured. For instance, to measure a glucose level, glucose dehydrogenase or glucose oxidase may be used for the oxidoreductase, and potassium ferricyanide is used for the electron mediator.

As better shown in FIG. 5, the insulating film 24 covers most part of the working electrode 21 and the counter electrode 22. In the working electrode 21 and the counter electrode 22, the ends 21A and 22Aa, the portions 21B and 22a at which the reagent portion 23 is to be formed, and the portions 21C, 22C adjacent the pinch portion 6 are not covered by the insulating film 24 for exposure. The insulating film 24 is formed with a through-hole 24A corresponding in position to the island portion 22B of the counter electrode 22, so that a part of the island portion 22B is exposed, without being covered by the insulating film 24.

In the flow path 5, the sample is caused to flow by capillary action, and a reaction field is provided. As better shown in FIGS. 4 and 5, the flow path 5 extends in the longitudinal direction of the substrate to cross the end 21B of the working electrode 21 and the corner region 22a of the main line portion 22A. The reagent portion 23 is provided in the flow path 5.

As better shown in FIG. 1, the pinch portion 6 is utilized by the user for holding the biosensor X1 in mounting the biosensor X1 to the analytical apparatus 1 or detaching the biosensor X1 from the analytical apparatus 1. As shown in FIGS. 3 and 5, the pinch portion 6 is a recess having an arcuate side surface defined by cutouts 28, 38 and 48 of the same configuration formed in the substrate 2, the spacer 3 and the cover 4.

The analytical apparatus 1, with which the biosensor X1 is used, performs the analysis of a sample by an electrochemical method. As shown in FIGS. 1 and 2, the analytical apparatus includes a connector 10 to which the biosensor X1 is mounted, and an analysis circuit 13 for performing computation necessary for the analysis of a particular component in a sample based on the information from the connector 10. As shown in FIG. 2, the connector 10 includes a first and a second terminals 11 and 12. The first terminal 11 is to come into contact with the end 21A of the working electrode 21, whereas the second terminal 12 comes into contact with the end 22Aa of the counter electrode 22. The first terminal 11 and the analysis circuit 13 are electrically connected to each other through a signal line 14. On the signal line 14 is provided a current/voltage conversion amplifier 15. The current/voltage conversion amplifier 15 converts information, or current, obtained from the biosensor X1 into a voltage to be inputted into the analysis circuit 13. The second terminal 12 is connected to ground.

To analyze a sample with use of the biosensor X1, the biosensor X1 is mounted to the analytical apparatus 1, as shown in FIG. 1 for example, and then a sample (typically blood or urine) is introduced through the sample inlet 50. The mounting of the biosensor X1 is performed in a manner such that the biosensor X1 is pinched at the pinch portions 6 by fingers, and then the biosensor X1 is inserted into the connector 10 of the analytical apparatus 1, with the shorter edge 25A (FIG. 3) leading ahead.

Figure 7:
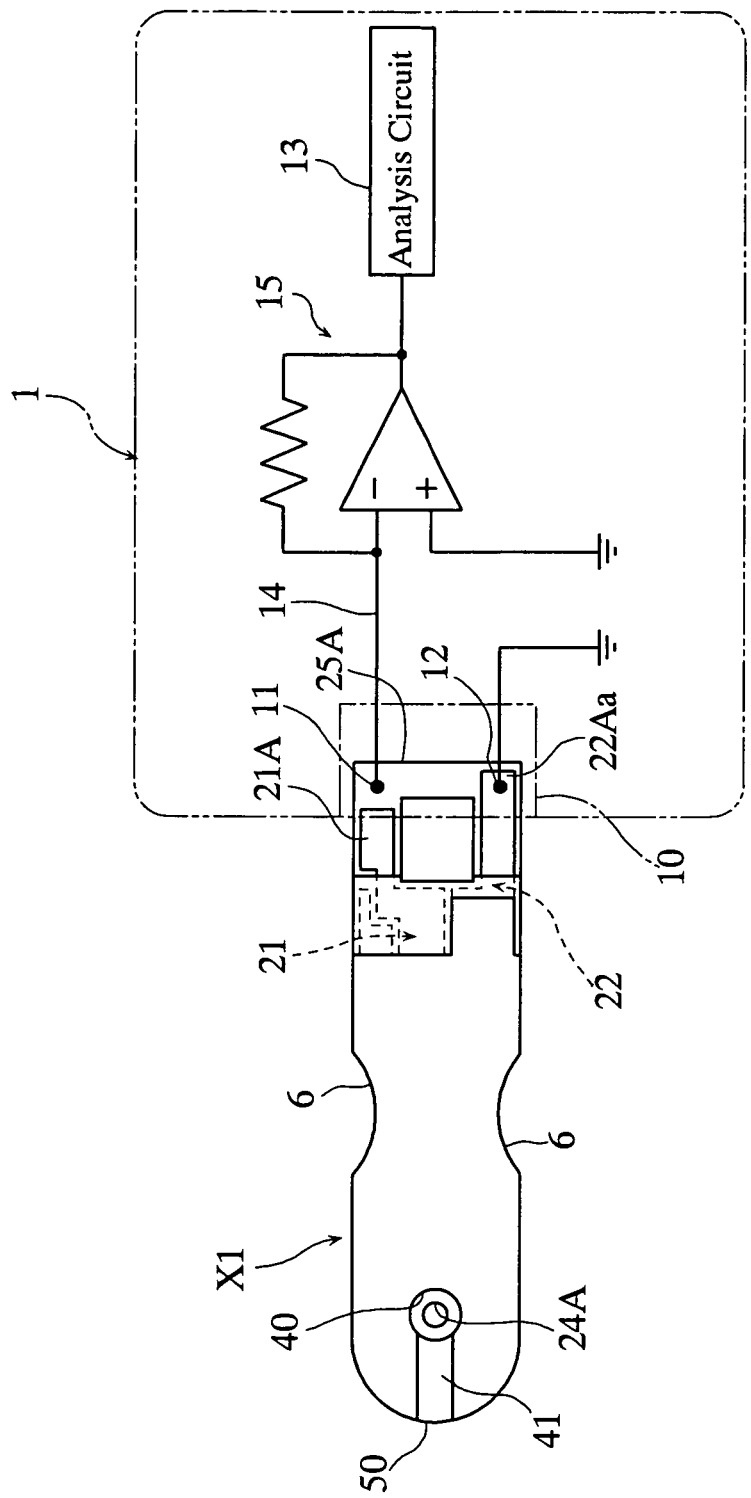
FIG. 7 is a schematic view showing the process of mounting the biosensor to the analytical apparatus, with the biosensor shown in plan and the analytical apparatus shown in block diagram.

As better shown in FIG. 2, when the biosensor X1 is mounted to the analytical apparatus 1, the ends 21A, 22Aa of the working electrode 21 and the counter electrode 22 come into contact with the first and the second terminals 11 and 12 of the analytical apparatus 1. The end 22Aa of the counter electrode 22 of the biosensor X1 is closer to the shorter edge 25A of the substrate 2 than the end 21A of the working electrode 21. Therefore, in mounting the biosensor X1 to the analytical apparatus 1, the end 22Aa of the counter electrode 22 comes into contact with the second terminal 12 as shown in FIG. 7, and then the end 21A of the working electrode 21 comes into contact with the first electrode 11 as shown in FIG. 2.

As will be understood from FIG. 4, the sample supplied to the biosensor X1 flows within the flow path 5 toward the air vent 40 by capillary action and thereby fills the flow path 5. The sample liquid dissolves the reagent portion 23 to produce a liquid phase reaction system in the flow path 5. As will be understood from FIG. 2, voltage is applied to the liquid phase reaction system by e.g. a DC power source (not shown) of the analytical apparatus 1 via the first and the second terminals 11, 12 of the analytical apparatus 1, the working electrode 21 and the counter electrode 22. The responsive current obtained is converted into a voltage by the current/voltage conversion amplifier 15 and then into a digital signal by a non-illustrated AD converter and inputted into the analysis circuit 13. Based on the digital signal corresponding to the responsive current, the analysis circuit 13 performs computation necessary for the analysis of the sample, such as the determination of the glucose level in blood.

As mentioned above, the biosensor X1 is disposable. Thus, after the computation at the analysis circuit 13 is completed, the biosensor X1 need be pulled out from the analytical apparatus 1. The pulling out of the biosensor X1 can be performed with the biosensor X1 pinched with fingers at the pinch portions 6.

In the biosensor X1, the pinch portion 6 of the biosensor X1 is utilized in mounting the biosensor X1 to the analytical apparatus 1 or in pulling the biosensor X1 out of the analytical apparatus 1. This means that, in the biosensor X1, the portion to be held by the user for mounting and detaching the biosensor X1 is predetermined. Accordingly, the biosensor X1 can be readily mounted and detached. Moreover, unintentional adhesion of the sample to the fingers is prevented in pulling out the biosensor X1, which is preferable for attaining good hygiene. Further, the pinch portion 6 is a recess, the slippage of fingers in mounting or detaching the biosensor X1 can be reduced. This feature also contributes to the improvement in usability of the biosensor X1.

As noted above, in mounting the biosensor X1 to the analytical apparatus 1, static electricity that has built up in a human body may be discharged to the working electrode 11 or the counter electrode 12 of the biosensor X1. Particularly, static electricity tends to be discharged to the working electrode 21 and the counter electrode 22 through the air vent 40. In the biosensor X1, the counter electrode 22 copes with the problem of such static electricity. Specifically, the island portion 22B of the counter electrode 22 is provided directly below the air vent 40 so that the static electricity coming through the air vent 40 is more likely to be conducted into the counter electrode 22 than into the working electrode 21. Since the counter electrode 22 is connected to ground through the second terminal 12 of the analytical apparatus 1, the static electricity inputted into the counter electrode 22 is dissipated, through the second terminal 12, to ground. As shown in FIG. 7, in mounting the biosensor X1 to the analytical apparatus 1, the end 22Aa of the counter electrode 22 comes into contact at an earlier stage than the end 21A of the working electrode 21. Thus, the removal of static electricity occurs when the end 22Aa of the counter electrode 22 comes into contact with the second terminal 12, while the end 21A of the working electrode 21 has not come into contact with the first terminal 11 yet. Then, when the end 21A of the working electrode 21 comes into contact with the first terminal 11, the static electricity has already been removed from the counter electrode 22. Therefore, the static electricity charged in the counter electrode 22 is prevented from being discharged to the working electrode 21 and being inputted into the analytical circuit 13.

Moreover, the pinch portion 6 is provided in the biosensor X1, and the counter electrode 22 is exposed from the insulating film 24 at a portion adjacent to the pinch portion 6. Therefore, even when static electricity is built up in the human body, the static electricity is likely to be inputted into the counter electrode 22 by mounting the biosensor X1 to the analytical apparatus 1 while holding the pinch portion 6. As a result, the static electricity in the human body is discharged through the counter electrode 22 without being inputted into the working electrode 21 and the analysis circuit 13.

With use of the biosensor X1, as described above, static electricity is prevented from flowing into the analysis circuit 13 through the working electrode 21 and the first terminal 11 of the analytical apparatus 1. Therefore, it is possible to prevent measurement failure or measurement error due to the static electricity into the analysis circuit 13. Further, the generation of Joule heat at the working electrode 21 due to static electricity can be prevented, whereby the working electrode 21 does not melt at a portion contacting the first terminal 11 of the analytical apparatus 1. These advantages are obtained simply by contriving the form of the counter electrode 22 of the biosensor X1, i.e., without changing the design of the analytical apparatus 1. Thus, it is advantageous that in coping with the disturbing noise, the structure of the analytical apparatus 1 does not become complicated, and the size of the analytical apparatus 1 does not become larger. In an instance where the working electrode 21 and the counter electrode 22 are formed by screen printing, the modification of the electrode can be performed simply by changing the configuration of the opening in a mask. Therefore, the countermeasure against the disturbing noise such as static electricity can be provided without changing the design of the existing manufacturing line, but with a slight increase of the material. This is advantageous in terms of the manufacturing cost. It should be noted that the biosensor X1 removes not only the static electricity coming from a human body but also other disturbing noise.

In the biosensor X1 of the above embodiment, the island portion 22B of the counter electrode 22 can be dispensed with, and disturbing noise can be coped with only by the main line portion 22A.

Next, biosensors according to second through sixth embodiments of the present invention will be described with reference to FIG. 8 through FIG. 13. In these figures, the elements which are identical or similar to those of the biosensor X1 or the analytical apparatus 1 of the first embodiment (See FIGS. 1-7) are designated by the same reference signs as those used above and description thereof will be omitted.

Figure 8:
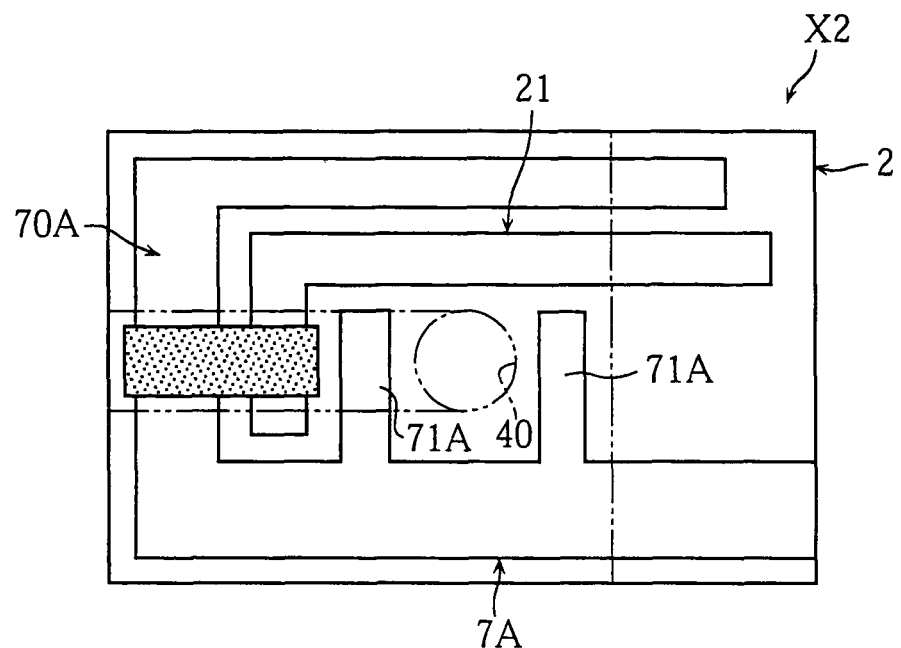
FIG. 8 is a transparent plan view showing a biosensor according to a second embodiment of the present invention.

FIG. 8 is a transparent plan view showing a biosensor according to the second embodiment of the present invention.

As shown in FIG. 8, the biosensor X2 differs from the above-described biosensor X1 of the first embodiment (See particularly FIG. 6) in structure of the counter electrode 7A.

The counter electrode 7A serves as a disturbing-noise countermeasure electrode, and includes a main line portion 70A and a pair of branches 71A. As viewed in plan, the paired branches 71A are arranged at the periphery of the air vent 40 and spaced from each other in the longitudinal direction of the substrate 2. As a result, as viewed in plan, the counter electrode 7A, together with the working electrode 21, surrounds the air vent 40.

With such a structure, the counter electrode 7A can effectively remove static electricity. Particularly, by the provision of the paired branches 71A, the static electricity coming through the air vent 40 can be discharged at the counter electrode 7A.

In the biosensor X2, one of the paired branches 71A may be dispensed with.

Figure 9:
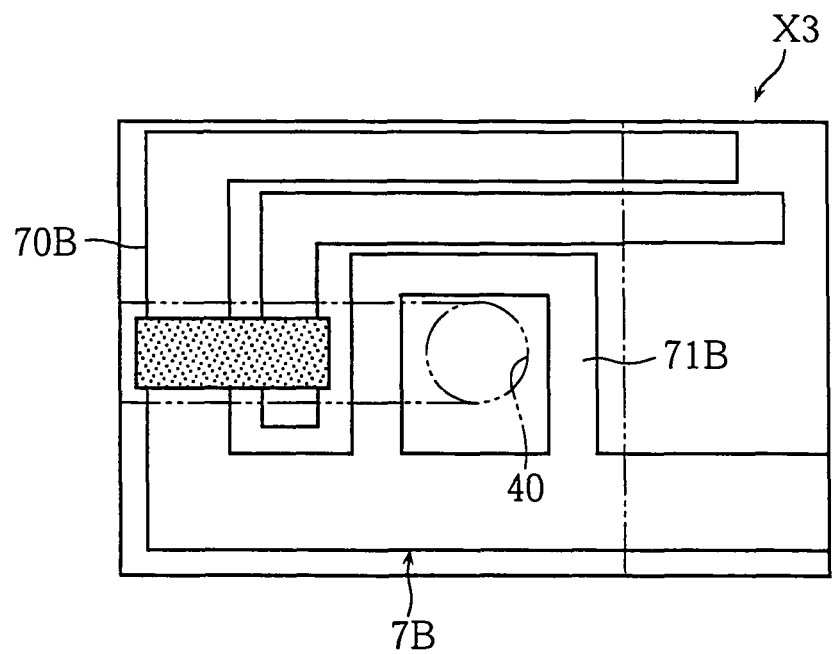
FIG. 9 is a transparent plan view showing a biosensor according to a third embodiment of the present invention.

FIG. 9 is a transparent plan view showing a biosensor according to the third embodiment of the present invention.

As shown in FIG. 9, the biosensor X3 is similar to the biosensor X2 (See FIG. 8) according to the second embodiment of the present invention. The counter electrode 7B of the biosensor X3 includes a main line portion 70B and a loop portion 71B. The loop portion 71B extends out from the main line portion 70B so as to surround the air vent 40.

Figure 10:
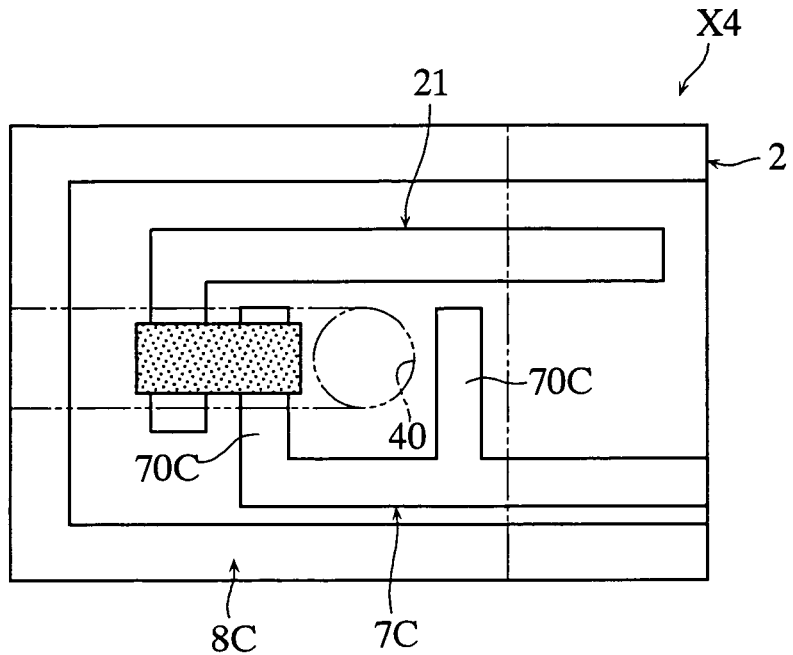
FIG. 10 is a transparent plan view showing a biosensor according to a fourth embodiment of the present invention.
Figure 11:
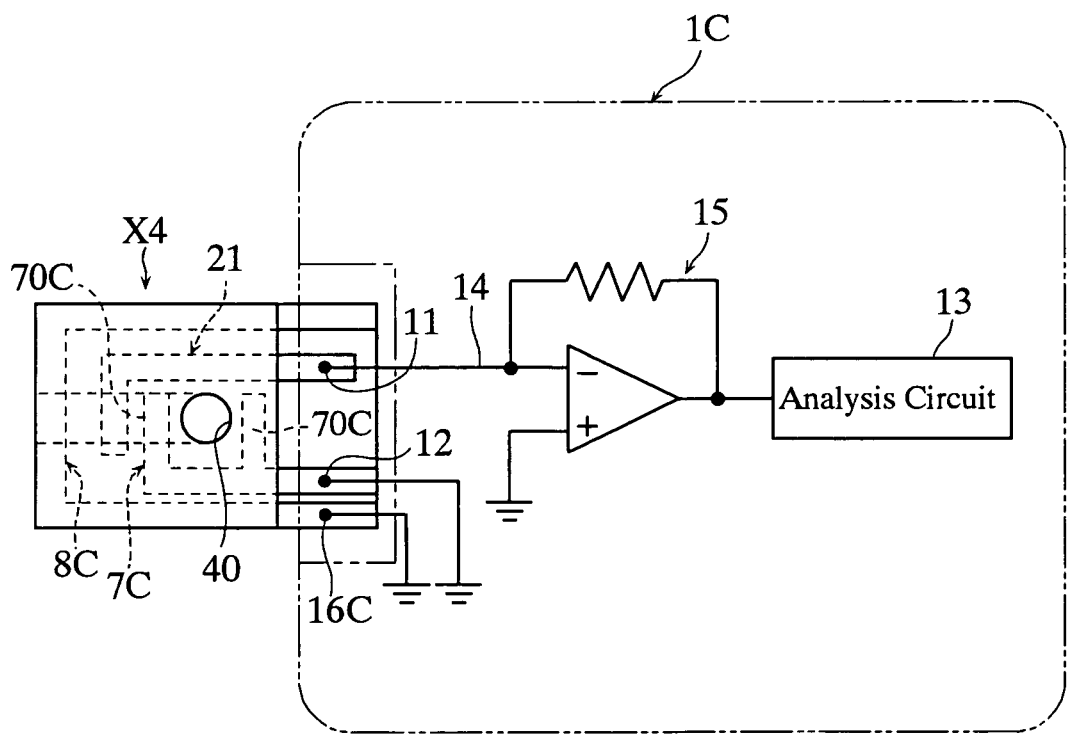
FIG. 11 is a schematic view showing the state in which the biosensor shown in FIG. 10 is mounted to the analytical apparatus, with the analytical apparatus shown in circuit block diagram and the biosensor shown in plan view.

FIGS. 10 and 11 show a biosensor according to the fourth embodiment of the present invention. FIG. 10 is a transparent plan view of the biosensor. FIG. 11 shows the biosensor in a plan view and the analytical apparatus in a circuit block diagram.

As shown in FIGS. 10 and 11, the biosensor X4 includes a working electrode 21, a counter electrode 7C and an additional electrode 8C. The counter electrode 7C has an F-shaped configuration including a pair of branches 70C arranged at the periphery of the air vent 40. The additional electrode 8C extends along the periphery of the substrate 2 and is U-shaped to surround the working electrode 21 and the counter electrode 7C.

As shown in FIG. 11, in addition to the first and the second terminals 11 and 12, the analytical apparatus 1C includes a third terminal 16C for coming into contact with the additional electrode 8C. The third terminal 16C is connected to ground separately from the second terminal 12.

Although the second terminal 12 and the third terminal 16C are connected to ground separately from each other in FIG. 11, these terminals 12 and 16C may be collectively connected to ground.

With the above structure, in addition to the counter electrode 7C, the additional electrode 8C also serves as a disturbing-noise countermeasure electrode. Specifically, the counter electrode 7C solely copes with the disturbing noise such as static electricity coming through the air vent 40, whereas the additional electrode 8C solely copes with the disturbing noise such as static electricity coming through a side surface of the biosensor X4. The counter electrode 7C and the additional electrode 8C are connected to ground when the biosensor X4 is mounted to the analytical apparatus 1C. Therefore, disturbing noise is dissipated to ground through the counter electrode 7C and the additional electrode 8C. In this manner, the input of disturbing noise into the working electrode 21, and hence, into the analysis circuit 13 can be properly prevented.

Figure 12:
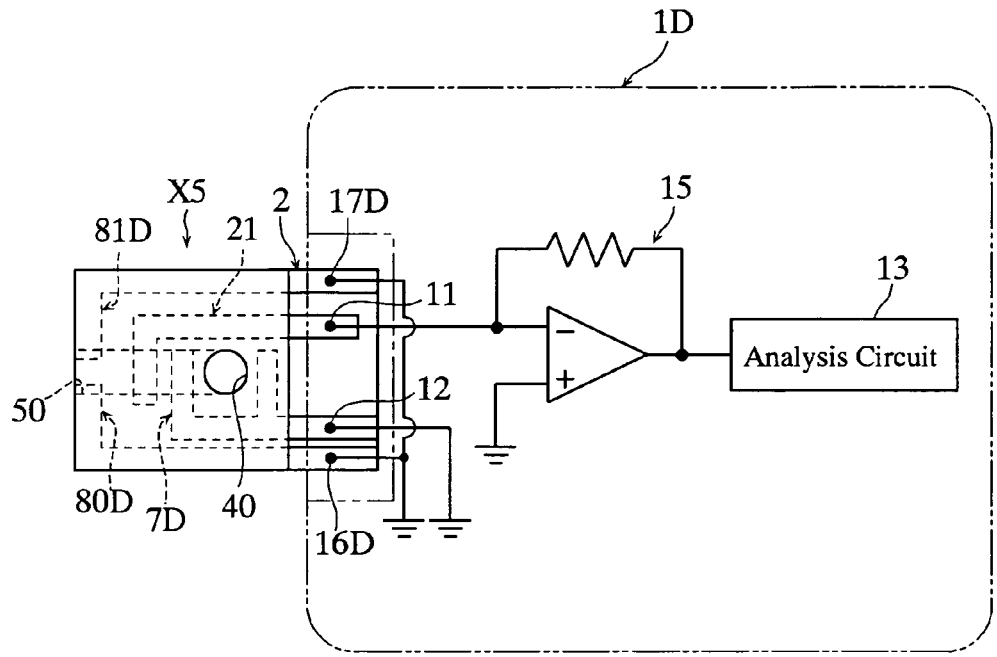
FIG. 12 is a schematic view showing a biosensor according to a fifth embodiment of the present invention, with the biosensor shown in plan view and the analytical apparatus shown in circuit block diagram.

FIG. 12 is a view for illustrating a biosensor according to the fifth embodiment of the present invention, with the biosensor and the analytical apparatus shown in plan view and in circuit block diagram, respectively.

The biosensor X5 shown in FIG. 12 includes two additional electrodes 80D and 81D in addition to the working electrode 21 and the counter electrode 7D. The structures of the working electrode 21 and the counter electrode 7D are similar to those of the foregoing biosensor X4 (See FIGS. 10 and 11). The two additional electrodes 80D and 81D have a configuration obtained by dividing the above-described additional electrode 8C (See FIGS. 10 and 11) at the sample inlet 50. Specifically, each of the additional electrodes 80D and 81D is L-shaped, extending along the periphery of the substrate. Accordingly, the analytical apparatus 1D includes a third and a fourth terminals 16D and 17D for coming into contact with the two additional electrodes 80D and 81D. The terminals 16D and 17D are collectively connected to ground.

With the above structure, in addition to the counter electrode 7D, the two additional electrodes 80D and 81D also serve as disturbing-noise countermeasure electrodes. The counter electrode 7D copes with the disturbing noise such as static electricity coming through the air vent 40, whereas the two additional electrodes 80D and 81D cope with the disturbing noise such as static electricity coming from the periphery of the biosensor X4.

Figure 13:
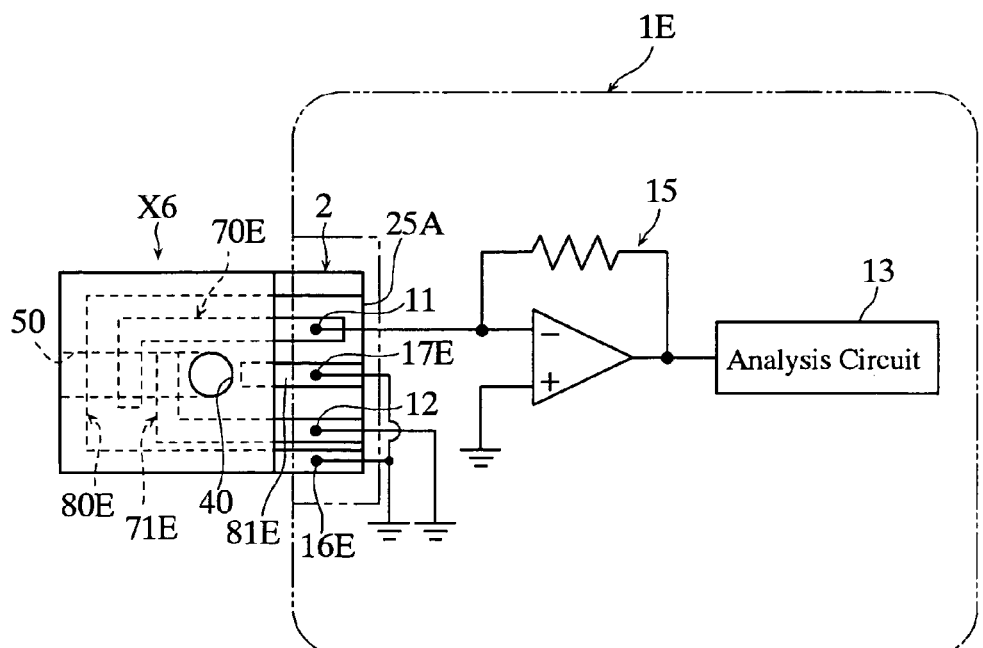
FIG. 13 is a schematic view showing a biosensor according to a sixth embodiment of the present invention, with the biosensor shown in plan view and the analytical apparatus shown in circuit block diagram.

FIG. 13 is a view for illustrating a biosensor according to the sixth embodiment of the present invention, with the biosensor and the analytical apparatus shown in plan view and in circuit block diagram, respectively.

Figure 14:
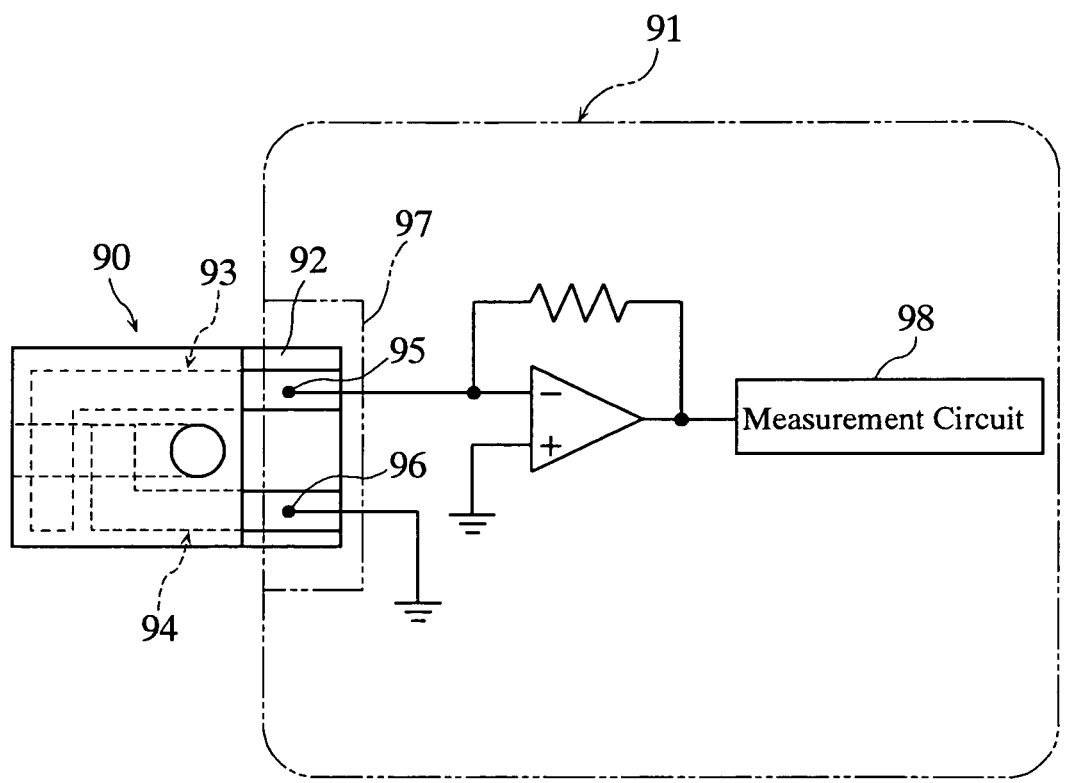
FIG. 14 is a schematic view for illustrating a conventional portable blood glucose level measuring apparatus and a biosensor.

The biosensor X6 shown in FIG. 13 includes two additional electrodes 80E and 81E in addition to the working electrodes 70E and 71E which are similar in structure to those of the prior art biosensor 90 shown in FIG. 14. The additional electrode 80E has a configuration similar to that of the additional electrode 8C (See FIGS. 10 and 11) of the above-described biosensor X4. Specifically, the additional electrode 80E is U-shaped, extending along the periphery of the substrate 2. The additional electrode 81E extends from the air vent 40 to a shorter edge 25A of the substrate 2 in the longitudinal direction of the substrate 2.

The analytical apparatus 1E includes a third and a fourth terminals 16E and 17E for coming into contact with the two additional electrodes 80E and 81E. The third and the fourth terminals 16E and 17E are collectively connected to ground.

In the biosensor X6 shown in FIG. 13 again, the additional electrode 80E be divided at the sample inlet 50, as is in the biosensor X5 shown in FIG. 12.

The present invention is not limited to the first through the sixth embodiments described above and may be modified in various ways. Particularly, the number and configuration of disturbing-noise countermeasure electrodes are not limited to the above-described examples and may be modified in various ways.

Although the biosensor for measuring a single item is exemplarily described in the foregoing embodiments, the present invention is also applicable to an electrochemical sensor designed for measuring a plurality of items such as a glucose level and a cholesterol level in blood.

In the foregoing embodiments, disturbing noise such as static electricity is removed by dissipation to ground. However, an electronic part or an electric circuit of power consumption may be provided in the analytical apparatus so that disturbing noise can be removed by these components.

The invention claimed is:

1. An analytical tool to be mounted to an analytical apparatus which includes a plurality of terminals and an analysis circuit, the analytical tool comprising:

an elongate substrate including a first end edge, a second end edge opposite to the first end edge, a first longitudinal edge, and a second longitudinal edge opposite to the first longitudinal edge;

a plurality of electrodes formed on the substrate for coming, into contact with the plurality of terminals when mounted to the analytical apparatus, each of the electrodes extending along the substrate between the first end edge and the second end edge;

a reagent portion formed on the substrate adjacent the first end edge of the substrate;

a flow path for moving a sample; and an air vent for discharging air from the flow path;

wherein at least one of the electrodes serves as a disturbing-noise countermeasure electrode to which disturbing noise is more likely to come in comparison with the electrode or electrodes other than said at least one of the electrodes, another of the electrodes serving as a working electrode;

wherein the disturbing-noise countermeasure electrode includes a first exposed end located adjacent to the second end edge of the substrate, a first main line portion extending from the first exposed end toward the first end edge of the substrate along the first longitudinal edge of the substrate, a second main line portion extending from the first main line portion toward the second longitudinal edge of the substrate along the first end edge of the substrate, and a third main line portion extending from the second main line portion toward the second end edge of the substrate along the second longitudinal edge of the substrate;

wherein the working electrode includes a second exposed end located adjacent to the second end edge of the substrate and extends from the second exposed end toward the first end edge of the substrate between the first and third main line portions of the disturbing-noise countermeasure electrode;

wherein the disturbing-noise countermeasure electrode includes a noise inputting exposed portion for allowing input of static electricity;

wherein the reagent portion bridges between the working electrode and the second main line portion of the disturbing-noise countermeasure electrode;

wherein the noise inputting exposed portion of the disturbing-noise countermeasure electrode is exposed through the air vent;

wherein the disturbing-noise countermeasure electrode further includes an island provided directly below the air vent and partially covered by an insulating film; and wherein the insulating film includes an opening for partially exposing the island to serve as the noise inputting exposed portion.

* * * * *